United States Patent [19]

Chauvin et al.

[11] Patent Number: 5,095,162
[45] Date of Patent: Mar. 10, 1992

[54] CATALYTIC COMPOSITION AND ITS USE IN OLIGOMERIZING MONOOLEFINS

[75] Inventors: Yves Chauvin, Le Pecq; Dominique Commereuc, Meudon; Alain Forestiere, Vernaison; Gérard Leger, Ecully, all of France

[73] Assignee: Institut Francais du Petrole, Rueil-Malmaison, France

[21] Appl. No.: 732,001

[22] Filed: Jul. 18, 1991

Related U.S. Application Data

[62] Division of Ser. No. 560,960, Aug. 1, 1990, Pat. No. 5,059,571.

[30] Foreign Application Priority Data

Aug. 8, 1989 [FR] France ............... 89 10758

[51] Int. Cl.$^5$ ............................................. C07C 2/24
[52] U.S. Cl. .................................. 585/512; 585/511; 585/514; 585/520; 585/531; 585/532
[58] Field of Search ............... 585/511, 512, 514, 520, 585/531, 532

[56] References Cited

U.S. PATENT DOCUMENTS

| | | | |
|---|---|---|---|
| 4,025,570 | 5/1977 | Cramer | 585/508 |
| 4,028,429 | 6/1977 | Cramer | 585/509 |
| 4,283,305 | 8/1981 | Chauvin et al. | 585/512 |
| 4,362,650 | 12/1982 | Chauvin et al. | 585/512 |
| 4,366,087 | 12/1982 | Le Pennec et al. | 502/117 |
| 4,387,262 | 6/1983 | Chauvin et al. | 585/512 |
| 4,476,341 | 10/1984 | Mathys | 585/512 |
| 4,777,314 | 10/1988 | Provin et al. | 585/531 |

Primary Examiner—Patrick P. Garvin
Assistant Examiner—E. D. Irzinski
Attorney, Agent, or Firm—Millen, White & Zelano

[57] ABSTRACT

The invention concerns a catalytic composition resulting from placing at least one divalent nickel compound into contact with at least one hydrocarbylaluminum halide and at least one epoxy compound, in any order. It also concerns the use of the catalytic composition in a process of oligomerizing monoolefins.

8 Claims, No Drawings

CATALYTIC COMPOSITION AND ITS USE IN OLIGOMERIZING MONOOLEFINS

This is a division of application Ser. No. 07/560,960 filed Aug. 1, 1990 and now U.S. Pat. No. 5,059,571.

BACKGROUND OF THE INVENTION

The subject of the invention is a new catalytic composition and its use in oligomerizing, particularly dimerizing and trimerizing, monoolefins. More specifically, it concerns combinations obtained by placing at least one divalent nickel compound into contact with at least one hydrocarbylaluminum halide and at least one apoxy compound (also described as oxirane), in any order.

It is well known to prepare catalysts for dimerizing or codimerizing monoolefins, such as ethylene, propylene or n-butenes. Such catalysts may e.g. result from: interaction between halides of $\pi$-allyl nickel phosphine and Lewis acids (FR-B-1 410 430), interaction between halides of nickel phosphine and Lewis acids (U.S. Pat. No. 3,485,881) or interaction between certain nickel carboxylates and hydrocarbylaluminum halides (U.S. Pat. No. 3,321,546). Other catalysts use zerovalent nickel compounds, though these are impractical because of their instability and high cost. It is generally preferable to use nickel compounds which are soluble in hydrocarbon materials.

Industrial application of the catalytic compositions described above to olefin cuts such as those emanating from petrochemical processes, such as catalytic or steam cracking, is encumbered by difficulties, particularly in connection with the impurities contained in the cuts.

These difficulties have been partly overcome by using improved catalytic formulations incorporating a divalent nickel compound, a hydrocarbylaluminum halide and a compound of the nature of a Bronsted acid (U.S. Pat. No. 4,283,305), or a combined compound of nickel in association with an alkylaluminum compound (U.S. Pat. Nos. 4,316,851, 4,366,087 and 4,398,049). These improved catalytic formulations usually include a halocarboxylic acid or the corresponding anion.

SUMMARY OF THE INVENTION

It has been found, unexpectedly, that if at least one divalent nickel compound is placed into contact with at least one hydrocarbylaluminum halide and at least one epoxy compound, this will lead to a catalytic composition more active than prior art formulations, and the composition will have the same properties in connection with any impurities present in the oligomerization charges.

Nickel compounds which can be used in the invention include all divalent nickel compounds, preferably compounds which are soluble to over 0.1 g/l in a hydrocarbon medium (e.g. in heptane at $+20°$ C.) and more particularly in the reagents or reaction medium. They may e.g. comprise nickel acetylacetonate and/or nickel carboxylates of the general formula $(RCOO)_2 Ni$, where R is a hydrocarbyl radical, such as an alkyl, cycloalkyl, alkenyl, aryl, aralkyl or alkaryl radical containing up to 20 carbon atoms, preferably a hydrocarbyl radical with 5 to 20 carbon atoms. The two radicals R may together form an alkylene radical with 6 to 18 carbon atoms. Some non-restrictive examples of nickel compounds are the following divalent nickel salts: divalent nickel octoate, 2-ethyl hexanoate, stearate, oleate, naphthenate and adipate.

The hydroxycarbylaluminum halides are preferably of the general formula $AlR'_xX_y$ where R' represents a monovalent hydrocarbon group containing e.g. up to 12 carbon atoms, such as an alkyl, aryl, aralkyl, alkaryl or cycloalkyl group; X represents a halogen selected e.g. from chlorine, bromine and iodine, and X is preferably a chlorine atom; x is from 1 to 2, y is from 1 to 2 with $x+y=3$ and preferably $x=1$ and $y=2$. Some examples of such compounds of the formula $AlR'_xX_y$, are ethyl aluminum sesquichloride, dichloroethylaluminum, dichloroisobutylaluminum and chlorodiethylaluminum.

The epoxy compounds are preferably of the following general formula:

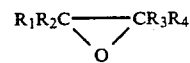

where $R_1$, $R_2$, $R_3$ and $R_4$ may be the same or different and are generally selected from the group formed by a hydrogen atom and hydrocarbon groups containing e.g. up to 12 carbon atoms, such as alkyl, aryl or cycloalkyl groups. Some examples of such compounds are ethylene oxide, propylene oxide, 1,2-epoxy butane and epoxy styrene. $R_1$ and $R_4$ may together form an alkylene radical with 4 to 10 carbon atoms, with $R_2$ and $R_3$ being defined as above as, for example, in 1,2-epoxy cyclohexane.

The three compounds included in the catalytic composition of the invention may be mixed in any order. However, it is preferable for the divalent nickel compound to be mixed with the epoxy compound first, at a temperature generally from $-10°$ to $+200°$ C. and preferably from $+20°$ to $+100°$ C., possibly in the presence of an aliphatic or aromatic hydrocarbon solvent. The mixture or composition thus obtained is then added to the oligomerization reaction medium simultaneously with or before the hydrocarbylaluminum halide.

The molar ratio of epoxy compound to divalent nickel compound is generally from 0.1:1 to 10:1 and preferably from 0.5:1 to 3:1. The molar ratio of hydrocarbylaluminum halide to divalent nickel compound is generally from 1:1 to 50:1 and preferably from 2:1 to 20:1.

The invention also concerns a process for oligomerizing monoolefins in the presence of the catalytic composition defined above, preferably at a temperature from $-20°$ to $+100°$ C., under pressure conditions such that the reagents are kept at least mostly in liquid phase.

Some examples of monoolefins which can be dimerized or oligomerized are ethylene, propylene, n-butenes and n-pentenes, either pure or in the form of mixtures such as those emanating from synthesizing processes such as catalytic or steam cracking. They may be cooligomerised with one another or with isobutene, for example ethylene with propylene and n-butenes, propylene with n-butenes or n-butenes with isobutene.

The concentration of the catalytic composition, expressed in nickel, in the liquid phase of the oligomerizing reaction is normally from 5 to 500 parts per million by weight.

The oligomerizing process may be applied particularly in a reactor with one or more reaction stages in series, with the olefin charge and/or the constituents of the catalytic system being introduced continuously, either at the first stage or at the first and at least any one other stage. On leaving the reactor the catalyst may be deactivated, e.g. with ammonia and/or an aqueous sodium hydroxide solution. Non-converted olefins and any alkanes present are then separated from the oligomers by distillation.

Alternatively, the oligomerization process may simply be carried out as a batch process.

The products obtained by the oligomerization process according to the invention may be used particularly as a fuel component for cars or as a charge in a hydroformylation process for synthesising aldehydes and alcohols.

The following examples illustrate the invention, but without restricting its scope.

EXAMPLE 1

100 g of a commercial solution of nickel 2-ethyl hexanoate in white spirit, containing 13% by weight of nickel, is placed in a stainless steel autoclave with a useful volume of 300 ml. The autoclave is closed and purged under vacuum, then connected to a bottle of ethylene oxide placed on a balance. The autoclave is heated to 70° C. and agitation is started. After 35 minutes, 9.7 g of ethylene oxide has been absorbed, corresponding to one equivalent per gram-atom of nickel. The autoclave is isolated and left to cool, then 100 ml of heptane is introduced with agitation. The solution obtained is drawn off, then evaporated under vacuum to give a viscous liquid with a nickel content of 13.45% by weight.

EXAMPLE 2

46 mg of the mixture prepared in Example 1, in solution in 5 ml of heptane, i.e. $1.05 \times 10^{-4}$ gram-atoms of nickel, is placed in a stainless steel autoclave with a useful volume of 250 ml, which has previously been dried and purged with argon. The next material injected is 100 g of an 11.5% by weight solution of propylene in a mixture of isohexenes emanating from a previous operation for dimerizing propylene. The temperature is set to 40° C. by circulating water in the double jacket of the autoclave, after which 0.2 g of dichloroethylaluminum is injected, in the form of a commercial 50% by weight solution in hexane. The development of the reaction is followed by taking samples from the autoclave at regular intervals of time. After 10 minutes' reaction the propylene is 66.1% converted to oligomers.

EXAMPLE 3 (comparative)

This example illustrates the result obtained with a prior art catalyst.

The apparatus and mode of operation are the same as those described in Example 2, except that the material first placed in the autoclave is not the mixture prepared in Example 1 but 47.6 mg of a commercial solution of nickel 2-ethyl hexanoate in white spirit containing 13% by weight of nickel, i.e. $1.05 \times 10^{-4}$ gram-atom of nickel. Under the same conditions as in Example 2 (particularly an injection of dichloroethylaluminum), the propylene is 24.1% converted to oligomers after 10 minutes' reaction.

EXAMPLE 4 (comparative)

This example illustrates the result obtained with an improved prior art catalytic composition.

The apparatus and mode of operation are the same as described in Example 2, except that the material first placed in the autoclave is not the mixture prepared in Example 1 but 62 mg of a solution of nickel 2-ethyl hexanoate in white spirit containing one equivalent of trifluoroacetic acid per gram-atom of nickel and with a nickel content of 10% (by weight) i.e. $1.05 \times 10^{-4}$ gram-atom of nickel. Under the same conditions as in Example 2 (particularly an injection of dichloroethylaluminum), the propylene is 58.9% converted to oligomers after 10 minutes' reaction.

EXAMPLE 5

272 mg of the mixture prepared in Example 1, in solution in 50 ml of heptane, is placed in the same apparatus as described in Example 2. 118 g of a $C_4$ cut containing 14.7% by weight of saturated hydrocarbons and 85.3% by weight of n-butenes is then injected. The temperature is again set to 40° C., then 1.18 g of dichloroethylaluminium is injected, in the form of a commercial 50% by weight solution in hexane. After 1 hour of reaction the n-butenes are 62.8% converted to oligomers.

EXAMPLE 6

A mixture of nickel 2-ethyl hexanoate and ethylene oxide is prepared by the procedure described in Example 1, except that 29.1 g of ethylene oxide is absorbed per 100 g of nickel salt containing 13% by weight of nickel. When the treatment described in Example 1 has been followed, the mixture obtained has a nickel content of 11.47% by weight.

EXAMPLE 7

The apparatus and mode of operation are the same as those described in Example 5, except that the material first placed in the autoclave is not the mixture prepared in Example 1 but 319 mg of the mixture prepared in Example 6, in solution in 5 ml of heptane. Under the same conditions as in Example 5 (paticularly an injection of dichloroethylaluminum), the n-butenes are 60.1% converted to oligomers after 1 hour of reaction.

EXAMPLE 8

100 g of a commercial solution of nickel 2-ethyl hexanoate in white spirit, containing 13% by weight of nickel, then 100 ml of heptane are placed in a stainless steel autoclave with a useful volume of 250 ml. 10 g of ethylene oxide is placed in a sieve connected to the autoclave, then forced into the autoclave by an excess pressure of 2 bars of nitrogen. The mixture is heated for 9 hours at 70° C. When the heptane has cooled and evaporated under vacuum, a viscous liquid is obtained with a nickel content of 13% by weight.

EXAMPLE 9

The reactor is fitted with an external recirculation loop equipped with an exchanger to control temperature, with a total volume of 7.6 liters. 1000 g/h of a charge made up of 75% of n-butenes, 6% of isobutene and 19% of butanes is injected continuously into the reactor. 2 separate streams are also injected continuously: (a) 20 g/h of a solution in heptane of the mixture prepared in Example 8, containing 21.45 g of mixture extended to 1000 g of solution and (b) 30 g/h of a solution in heptane containing 6% by weight of dichloroethylaluminum. The temperature is fixed at 42° C.

On leaving the reactor the effluent is destroyed continuously by successive injections of ammonia gas and a 15% by weight aqueous solution of sodium hydroxide.

Analysis of the effluent shows there to be 76.4% conversion of the n-butenes and 72.2% conversion of the isobutene. The composition of the effluent (by weight) is 85.2% of octenes, 10.8% of dodecenes, 2% of hexadecenes and 2% of olefins higher than $C_{16}$. Selectivity for dimers, calculated in respect of the monomers converted, is 86.9% for n-butenes and 58.1% for isobutene.

EXAMPLE 10 (comparative)

This example illustrates the result obtained with a prior art catalytic composition.

The same apparatus is used continuously, and the same operating conditions are used as described in Example 9, except that the stream of solution of the mixture prepared in Example 8 is replaced by a 20 g/h stream of a solution in heptane of nickel 2-ethyl hexanoate, containing one equivalent of trifluoroacetic acid per gram-atom of nickel and 0.28% (by weight) of nickel; this corresponds to the same hourly quantity of nickel as in Example 9.

Analysis of the effluent shows there to be 72.6% conversion of the n-butenes and 90.9% conversion of the isobutene. The composition of the effluent (by weight) is 78.6% of octenes, 13.1% of dodecenes, 4.3% of hexadecenes and 4% of olefins higher than $C_{16}$. Selectivity for dimers, calculated in respect of the monomers converted, is 83.7% for n-butenes and 22.8% for isobutene.

We claim:

1. In a process for oligomerizing olefins in the presence of a catalyst composition, the improvement wherein the catalyst composition results from placing at least one divalent nickel compound into contact with at least one hydrocarbylaluminum halide and at least one epoxy compound in any order wherein the molar ratio of hydrocarbylaluminium halide to divalent nickel compound is from 1:1 to 50:1, and the molar ratio of epoxy compound to divalent nickel compound is from 0.1:1 to 10:1.

2. A process according to claim 1, wherein the epoxy compound is of the following formula:

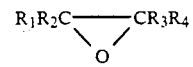

where $R_1$, $R_2$, $R_3$ and $R_4$ are the same or different and represent a hydrogen atom or hydrocarbon groups containing up to 12 carbon atoms, or $R_1$ and $R_4$ together form an alkylene radical having 4 to 10 carbon atoms.

3. A process according to claim 2, wherein the epoxy compound is ethylene oxide, propylene oxide, 1,2-epoxy butane, epoxy styrene or 1,2-epoxy cyclohexane.

4. A process according to claim 1, wherein the hydrocarbylaluminium halide is of the formula $AlR'_xX_y$ where R' represents a monovalent hydrocarbon group, X represents chlorine, bromine or iodine, x is from 1 to 2; y is from 1 to 2, and $x+y=3$.

5. A process according to claim 4, wherein in the general formula for the hydrocarbylaluminium halide, $x=1$, $y=2$ and X represents chlorine.

6. A process according to claim 1, wherein the divalent nickel compound is nickel acetylacetonate or a nickel carboxylate of the formula $(RCOO)_2Ni$ where R is a hydrocarbyl radical having 5 to 20 carbon atoms or the two R's together form an alkylene radical having 6 to 18 carbon atoms.

7. A process according to claim 1, wherein the molar ratio of epoxy compound to divalent nickel compound is from 0.5:1 to 3:1.

8. A process according to claim 1, wherein the molar ratio of hydrocarbylaluminium halide to divalent nickel compound is from 2:1 to 20:1, and the molar ratio of epoxy compound divalent nickel compound is from 0.5:1 to 3:1.

* * * * *